US010501466B2

(12) United States Patent
Fesik et al.

(10) Patent No.: US 10,501,466 B2
(45) Date of Patent: Dec. 10, 2019

(54) WDR5 INHIBITORS AND MODULATORS

(71) Applicant: Vanderbilt University, Nashville, TN (US)

(72) Inventors: Stephen W. Fesik, Nashville, TN (US); Shaun R. Stauffer, Brentwood, TN (US); James M. Salovich, Nashville, TN (US); William P. Tansey, Brentwood, TN (US); Feng Wang, Nashville, TN (US); Jason Phan, Nashville, TN (US); Edward T. Olejniczak, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/135,729

(22) Filed: Sep. 19, 2018

(65) Prior Publication Data

US 2019/0084988 A1    Mar. 21, 2019

Related U.S. Application Data

(60) Provisional application No. 62/560,496, filed on Sep. 19, 2017.

(51) Int. Cl.
  *C07D 487/04* (2006.01)
  *A61P 35/02* (2006.01)

(52) U.S. Cl.
  CPC ............ *C07D 487/04* (2013.01); *A61P 35/02* (2018.01)

(58) Field of Classification Search
  CPC .............................. C07D 487/04; A61P 35/02
  See application file for complete search history.

(56) References Cited

U.S. PATENT DOCUMENTS

| 1,016,076 A1 | 12/2018 | Fesik et al. |
| 2010/0022002 A1 | 1/2010 | Cosgrove et al. |
| 2013/0203167 A1 | 8/2013 | Cosgrove et al. |
| 2018/0086767 A1 | 3/2018 | Fesik et al. |

FOREIGN PATENT DOCUMENTS

| WO | WO2011159685 | 12/2011 |
| WO | WO2013082017 | 6/2013 |
| WO | 2017147700 A1 | 9/2017 |
| WO | 2017147701 A1 | 9/2017 |
| WO | 2019046944 A1 | 3/2019 |

OTHER PUBLICATIONS

Guarnaccia, J Clin Med, Jan. 2018, vol. 7(21), 1-17. (Year: 2018).*
Aho, Cell Reports, vol. 26, 2916-2928, 2019. (Year: 2019).*
Ansel, Introduction to Pharmaceutical Dosage Forms, 2nd Ed., 1976, 5 pages.
Balgobiind et al., "The heterogeneity of pediatric MLL-rearranged acute myeloid leukemia," Leukemia, 2011, 8, 1239-1248.
Butler et al., "The HRX Proto-oncogene Product is Widely Expressed in Human Tissues and Localizes to Nuclear Structures." Blood, 1997, 89:3361-3370.
C.T.F.A. Cosmetic Ingredient Handbook, 1992, pp. 587-592.
Cambridge Healthtech Institute, "14th Annual Discovery on Target," 2016 Plenary Keynote Program, 72 pages.
Cao et al. "Targeting MLL1 H3 K4 methyltransferase activity in MLL leukemia," Molecular Cell, 2014, 53, 247-261.
Carruthers, Some Modern Methods of Organic Synthesis, 3rd Edition, Cambridge University Press, Cambridge, 1987, 6 pages.
Carugo et al., "In Vivo Functional Platform Targeting Patient Derived Xenografts Identifies WDR5-Myc Association as a Critical Determinant of Pancreatic Cancer," Cell Reports, 2016, 16, 133-147.
Caslini et al., "Interaction of MLL Amino Terminal Sequences with Menin is Required for Transformation," Cancer Res., 2007, 67, 7275-83.
Chen et al., "Upregulated WDR5 promotes proliferation, self-renewal and chemoresistance in bladder cancer via mediating H3K4 trimethylation," Scientific Reports, 2015, 5:8293, 1-12.
Dai et al., "WDR5 Expression is Prognostic of Breast Cancer Outcome," PLoSOne, 2015, 10, PMC4565643.
Dias et al., "Structural analysis of the KANSL1/WDR5/KANSL2 complex reveals that WDR5 is required for efficient assembly and chromatin targeting of the NSL complex," Genes & Development, 2014, 28, 929-942.
DiMartino et al., "Mll rearrangements in human malignancies: lessons from clinical and biological studies," Br. J. Haematol. 1999, 106, 614-626.
EE et al., "An Embryonic Stem Cell-Specific NuRD Complex Functions through Interaction with WDR5," Stem Cell Reports, 2017, 8, 1488-96.
Furniss, Hannaford, Smith, and Tatchell, "Vogel's Textbook of Practical Organic Chemistry", 5th edition (1989), Longman Scientific & Technical, Essex CM20 2JE, England, 15 pages.
IUPAC 1974 Recommendations for Section E, Fundamental Stereochemistry, in Pure Appl. Chem., 1976; 45:13-30.
Karatas et al., "Analysis of the Binding of Mixed Lineage Leukemia 1 (MLL1) and Histone 3 Peptides to WD Repeat Domain 5 (WDR5) for the Design of Inhibitors of the MLL1—WDR5 Interaction," J. Med. Chem. 2010, 5179-5185.
Karatas et al., "Discovery of a Highly Potent, Cell-Permeable Macrocyclic Peptidomimetic (MM-589) Targeting the WD Repeat Domain 5 Protein (WDR5)—Mixed Lineage Leukemia (MLL) Protein—Protein Interaction," J. Med. Chem., 2017, 60, 4818-4839.
Karatas et al., "High-affinity, small-molecule peptidomimetic inhibitors of MLL1/WDR5 protein—protein interaction," J. Amer. Chem. Soc. 2013, 669-82.

(Continued)

*Primary Examiner* — D Margaret M Seaman
(74) *Attorney, Agent, or Firm* — Michael Best & Friedrich LLP

(57) ABSTRACT

Described are N-(6-(6,7-dihydro-5H-pyrrolo[1,2-a]imidazol-2-yl)-2,3-dihydro-1H-inden-1-yl)benzamide and acetamide-containing compounds that inhibit WDR5 and associated protein-protein interactions, pharmaceutical compositions including the compounds, and methods of using the compounds and compositions for treating disorders and conditions in a subject.

20 Claims, No Drawings

(56) References Cited

OTHER PUBLICATIONS

Larock, Comprehensive Organic Transformations, VCH Publishers, Inc., New York, 1989, 22 pages.
Li et al., "MOF and H4 K16 acetylation play important roles in DNA damage repair by modulating recruitment of DNA damage repair protein Mdc1.," Molecular and Cellular Biology, 2010, 30, 5335-47.
Lide, Periodic Table of the Elements, CAS version, Handbook of Chemistry and Physics, 75th Ed., 1979, 2 pages.
Lieberman et al., Pharmaceutical Dosage Forms: Tablets, 1981, 15 pages.
Marschalek, "Mechanisms of leukemogenesis by MLL fusion proteins," Br. J. Haematol. 2011, 152, 141-54.
McCutcheon's vol. 1, Emulsifiers & Detergents, North American Edition, 1994, pp. 236-239.
Milne et al., "Leukemogenic MLL Fusion Proteins Bind across a Broad Region of the Hox a9 Locus, Promoting Transcription and Multiple Histone Modifications," Cancer Res., 2005, 65, 11367-74.
Milne et al., "MLL Targets SET Domain Methyltransferase Activity to Hox Gene Promoters," Mol. Cell, 2002, 10, 1107-17.
Modern Pharmaceutics, Chapters 9 and 10, Banker & Rhodes, eds., 1979, 329-427.
Nakamura et al., "ALL-1 is a Histone Methyltransferase that Assembles a Supercomplex of Proteins Involved in Transcriptional Regulation," Mol. Cell, 2002, 10, 1119-28.
Organic Chemistry, Thomas Sorrell, University Science Books, Sausalito, 1999, 18 pages.
Patel et al., "On the Mechanism of Multiple Lysine Methylation by the Human Mixed Lineage Leukemia Protein-1 (MLL1) Core Complex," J. Biol. Chem., 2009, 284, 24242-56.
PGM Wuts and TW Greene, in Greene's book titled Protective Groups in Organic Synthesis (4th ed.), John Wiley & Sons, NY, 2006, 4 pages.
Pigazzi et al., "MLL partner genes drive distinct gene expression profiles and genomic alterations in pediatric acute myeloid leukemia: an AIEOP study," Leukemia, 2011, 25, 560-563.
Pui et al., "Clinical heterogeneity in childhood acute lymphoblastic leukemia with 11q23 rearrangements," Leukemia, 2003, 4, 700-706.
Remington's Pharmaceutical Sciences, 15th Ed. 1975, pp. 335-337.
Robak et al., "Synthesis and applications of tert-butanesulfinamide." Chem. Rev., 2010; 110:3600-3740.
Senisterra et al., "Small-molecule inhibition of MLL activity by disruption of its interaction with WDR5." Biochem. J., 2013, 449, 151-159.
Slany, "The molecular biology of mixed lineage leukemia," Haematologica, 2009, 94, 984-993.
Smith and March March's Advanced Organic Chemistry, 5th Edition, John Wiley & Sons, Inc., New York, 2001, 3 pages.
Song et al., "Neurofurans, novel indices of oxidant stress derived from docosahexaenoic acid," J. Biol. Chem. 2008, 283, 35258-64.
Sun et al., "WDR5 Supports an N-Myc Transcriptional Complex That Drives a Protumorigenic Gene Expression Signature in Neuroblastoma," Cancer Research, 2015, 75, 5143-54.
Tamai etal., "11q23/MLL Acute Leukemia : Update of Clinical Aspects," J. Clin. Exp. Hematop., 2010, 50, 91-98.
Tan et al., "P13K/AKT-mediated upregulation of WDR5 promotes colorectal cancer metastasis by directly targeting ZNF407," Cell Death & Disease, 2017, 8, 1-12.
Tkachuk et al., "Involvement of a homolog of Drosophila trithorax by 11q23 chromosomal translocations in acute leukemias," Cell, 1992, 71, 691-700.
Thomas et al., "Interaction with WDR5 Promotes Target Gene Recognition and Tumorigenesis by Myc," Molecular Cell, 2015, 58, 440-52.
Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group," Leukemia, 2007, 21, 2258-63.
Yokoyama et al., "Leukemia proto-oncoprotein MLL forms a SET1-like histone methyltransferase complex with menin to regulate Hox gene expression," Mol. Cell Biol., 2004, 24, 5639-49.
Yokoyama et al., "The menin tumor suppressor protein is an essential oncogenic cofactor for MLL-associated leukemogenesis," Cell, 2005, 123, 207-18.
Yu et al., "MLL, a mammalian trithorax-group gene, functions as a transcriptional maintenance factor in morphogenesis," Proc. Natl. Acad. Sci., 1998, 95, 10632-10636.
Medline Plus, Cancer, Retrieved from the Internet 2007, URL : http://www.nlm.nih.gov/medlineplus/cancer.html.
Lala et al., "Role of nitric oxide in tumor progression: lessons from experimental tumors." Cancer and Metastasis Reviews. Mar. 1, 1998;17(1):91-106.
Golub et al., "Molecular classification of cancer: class discovery and class prediction by gene expression monitoring." Science. Oct. 15, 1999;286(5439):531-7.

* cited by examiner

WDR5 INHIBITORS AND MODULATORS

CROSS-REFERENCE TO RELATED APPLICATIONS

This application claims priority from U.S. Provisional Patent Application No. 62/560,496, filed Sep. 19, 2017, the entire contents of which being incorporated by reference in its entirety.

TECHNICAL FIELD

The present invention relates generally to compounds that inhibit the binding of transcription factors, regulatory regulators, and chromatin to WDR5 and methods of use thereof. In particular embodiments, the present invention provides compositions comprising N-(6-(6,7-dihydro-5H-pyrrolo[1,2-a]imidazol-2-yl)-2,3-dihydro-1H-inden-1-yl)benzamide and acetamide-containing compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizawa, D.; et. al. *Leukemia,* 2007, 21, 2258-63.) and 10% of all acute leukemia cases (Marschalek, R. *Br. J. Haematol.* 2011, 152, 141-54.). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia,* 2003, 4, 700-706.; Tomizawa, D.; et. al. *Leukemia,* 2007, 21, 2258-63.).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila trithorax* (Trx) (Thachuk, D. C.; et al. *Cell,* 1992, 71, 691-700.). Wild type MLL binds to regulatory regions of homeox (HOX) genes (Milne, T. A.; et al. *Cancer Res.,* 2005, 65, 11367-74.) through the amino terminal fragment while the catalytic C-terminal domain catalyzes the Histone 3 lysine 4 (H3K4) methylation via interaction with WDR5 and up regulates target gene transcription (Nakamura, T.; et al. *Mol. Cell,* 2002, 10, 1119-28; Yokoyama, A. et al. *Mol. Cell Biol.,* 2004, 24, 5639-49.; Milne, T. A.; et al. *Mol. Cell,* 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.,* 1998, 95, 10632-10636.). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia,* 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.,* 2007, 67, 7275-83.; Yokoyama, A.; et al. *Cell,* 2005, 123, 207-18.). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., *Haematologica,* 2009, 94, 984-993). Clinical studies reveal that MLL of different chromosomal translocations are associated with different prognosis and are treated differently under current protocols (Tamai, H., et al. *J. Clin. Exp. Hematop.,* 2010, 50, 91-98; Balgobind, B. V., et al. *Leukemia,* 2011, 8, 1239-1248; Pigazzi, M.; et al. Leukemia, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.,* 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell,* 2014, 53, 247-61., Karatas, H.; et al. *J. Med. Chem.,* 2017, 60, 4818-4839.). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other transcription factors/ epigenetic writers or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X., et al. Molecular and Cellular Biology, 2010, 30, 5335-47., Dias, J., et al. *Genes & Development,* 2014, 28, 929-942.), C/EBPα p30 (Senisterra, G., et al. *Biochem. J,* 2013, 449, 151-159.), c-MYC (Thomas, L. R.; et al. *Molecular Cell,* 2015, 58, 440-52., herein incorporated by reference in its entirety), and the NuRD complex (Ee, L.-S., et al. Stem Cell Reports, 2017, 8, 1488-96.). In addition, WDR5 expression levels have been reported to be correlative and connected to patient prognosis in several other cancer types, including neuroblastoma (Sun, Y. et al. *Cancer Research,* 2015, 75, 5143-54.), breast cancer (Dai, X. et al. *PLoSOne,* 2015, 10, PMC4565643), bladder cancer (Chen, X. et al. *Scientific Reports,* 2015, 5, 8293.), and colorectal cancer (Tan, X. et al. *Cell Death & Disease,* 2017, 8, PMC5386518). In addition, in an unbiased shRNA screen in human xenografts, WDR5 was identified as an important target in pancreatic cancer (Carugo, A. et al. *Cell Reports,* 2016, 16, 133-147.). Based on the growing number of complexes identified which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

In one aspect, disclosed is a compound of formula (I),

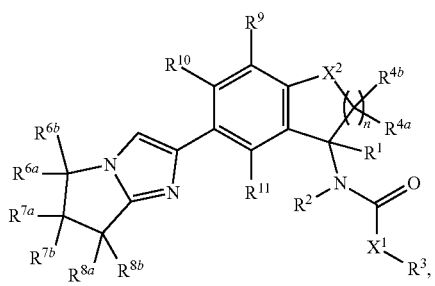

or a pharmaceutically acceptable salt thereof, wherein:

$R^1$ is hydrogen or $C_{1-4}$alkyl;

$R^2$ is hydrogen, $C_{1-6}$alkyl, $C_{3-8}$cycloalkyl, or $C_{3-8}$cycloalkyl-$C_{1-3}$alkylene-;

$X^1$ is a bond or —N($R^a$)—, wherein $R^a$ is hydrogen, $C_{1-4}$alkyl, or $C_{1-4}$haloalkyl;

$R^3$ is $C_{1-4}$alkyl, $G^1$, or -$L^1$-$G^2$;

$G^1$ and $G^2$ are $C_{3-8}$cycloalkyl, a 4- to 8-membered heterocyclyl, aryl, or heteroaryl, wherein $G^1$ and $G^2$ are optionally substituted with 1-5 substituents independently selected from the group consisting of halogen, cyano, $C_{1-4}$alkyl, $C_{1-4}$haloalkyl, —O—$C_{1-4}$alkyl, —O—$C_{1-4}$haloalkyl, OH, oxo, —C(O)$C_{1-4}$alkyl, —C(O)$C_{1-4}$haloalkyl, —NH$_2$, —NH($C_{1-4}$alkyl), —N($C_{1-4}$alkyl)$_2$, —NHC(O)$C_{1-4}$alkyl, and —N($C_{1-4}$alkyl)C(O)$C_{1-4}$alkyl;

$L^1$ is —$C_{1-3}$alkylene-;

$R^{4a}$, at each occurrence, is independently hydrogen, halogen, cyano, $C_{1-4}$alkyl, $C_{1-4}$haloalkyl, —O—$C_{1-4}$alkyl, or OH;

$R^{4b}$, at each occurrence, is independently hydrogen, halogen, or $C_{1-4}$alkyl; or $R^{4a}$ and $R^{4b}$ together with the carbon to which they are attached form a $C_{3-6}$cycloalkyl;

n is 1 or 2;

$X^2$ is C($R^{4a}$)($R^{4b}$), O, S, or N($R^5$);

$R^5$ is hydrogen, $C_{1-4}$alkyl, $C_{1-4}$haloalkyl, $C_{3-6}$cycloalkyl, $C_{3-6}$cycloalkyl-$C_{1-3}$alkylene-, —C(O)$C_{1-4}$alkyl, —C(O)$C_{3-6}$cycloalkyl, or —C(O)O$C_{1-4}$alkyl;

$R^{6a}$, $R^{6b}$, $R^{7a}$, $R^{7b}$, $R^{8a}$, and $R^{8b}$ are each independently selected from the group consisting of hydrogen, $C_{1-4}$alkyl, $C_{1-4}$haloalkyl, halo, and hydroxy; and $R^9$, $R^{10}$, and $R^{11}$ are each independently selected from the group consisting of hydrogen, halogen, cyano, $C_{1-4}$alkyl, $C_{1-4}$haloalkyl, —O—$C_{1-4}$alkyl, and —O—$C_{1-4}$haloalkyl.

Also disclosed are pharmaceutical compositions comprising the compounds, methods of making the compounds, and methods of using the compounds for inhibiting the binding of MLL1 to WDR5. Also disclosed are methods of treating cancer, comprising administration of a therapeutically effective amount of a compound of formula (I), or a pharmaceutically acceptable salt thereof to a subject in need thereof.

DETAILED DESCRIPTION

Disclosed herein are inhibitors of WDR5 which bind at the WDR5 interaction or WIN-site. The inhibitors can be compounds of formula (I). Compounds of formula (I) can be used to treat cancers associated with the MLL1-WDR5 interaction. In one aspect, disclosed are N-(6-(6,7-dihydro-5H-pyrrolo[1,2-a]imidazol-2-yl)-2,3-dihydro-1H-inden-1-yl)benzamide and acetamide-containing compounds as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_{1-6}$alkyl" means a straight or branched chain hydrocarbon containing from 1 to 6 carbon atoms. The term "$C_{1-3}$alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group as defined herein, or a heterocycle, as defined herein. Representative examples of aryl include, but are not limited to, indolyl, naphthyl, phenyl, and tetrahydroquinolinyl.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. A cycloalkyl may be monocyclic, bicyclic, or tricyclic. A cycloalkyl group may include one or more bridges in which two non-adjacent atoms are linked by an alkylene group of 1, 2, 3, or 4 carbon atoms, (e.g., norbornyl, adamantyl). Representative examples of cycloalkyl include, but are not limited to, cyclopropyl, cyclobutyl, cyclopentyl, cyclohexyl, cycloheptyl, cyclooctyl, cyclononyl, cyclodecyl, and adamantyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "---" designates a single bond (—) or a double bond (=).

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

Terms such as "alkyl," "cycloalkyl," "alkylene," etc. may be preceded by a designation indicating the number of atoms present in the group in a particular instance (e.g., "$C_{1-4}$ alkyl," "$C_3$-6cycloalkyl," "$C_{1-4}$alkylene"). These designations are used as generally understood by those skilled in the art. For example, the representation "C" followed by a subscripted number(s) indicates the number of carbon atoms present in the group that follows. Thus, "$C_3$alkyl" is an alkyl group with three carbon atoms (i.e., n-propyl, isopropyl). Where a range is given, as in "$C_1$-4," the members of the group that follows may have any number of carbon atoms falling within the recited range. A "$C_{1-4}$alkyl," for example, is an alkyl group having from 1 to 4 carbon atoms, however arranged (i.e., straight chain or branched).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I). Embodiments of formula (I) include the following descriptions of $X^1$, $X^2$, $R^1$, $R^2$, $R^3$, $R^{4a}$, $R^{4b}$, $R^{6a}$, $R^{6b}$, $R^{7a}$, $R^{7b}$, $R^{8a}$, $R^{8b}$, $R^9$, $R^{10}$, $R^{11}$, and n, and any combinations thereof.

In some embodiments, $R^9$, $R^{10}$, and $R^{11}$ are each hydrogen.

In some embodiments, $R^{4a}$ and $R^{4b}$ are each hydrogen.

In some embodiments, $R^{6a}$, $R^{6b}$, $R^{7a}$, $R^{7b}$, $R^{8a}$, and $R^{8b}$ are each hydrogen.

In some embodiments, n is 1.

In some embodiments, n is 2.

In some embodiments, $X^2$ is $CH_2$.

In some embodiments, $X^2$ is $NR^5$. In further embodiments, $R^5$ is —C(O)$C_{1-4}$alkyl.

In some embodiments, $R^2$ is hydrogen or $C_{3-8}$cycloalkyl-$C_{1-3}$alkylene- (e.g., cyclopropyl-$CH_2$—).

In some embodiments, $X^1$ is a bond.

In some embodiments, $R^3$ is $G^1$ or -$L^1$-$G^2$; $G^1$ is 4- to 8-membered heterocyclyl, aryl, or heteroaryl; and $G^2$ is aryl; wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl. In further embodiments, $G^1$ is a 4- to 8-membered heterocyclyl containing one heteroatom selected from nitrogen, oxygen, and sulfur; phenyl; or a 5- to 6-membered monocyclic heteroaryl; and $G^2$ is phenyl; wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl. For example, in some embodiments,

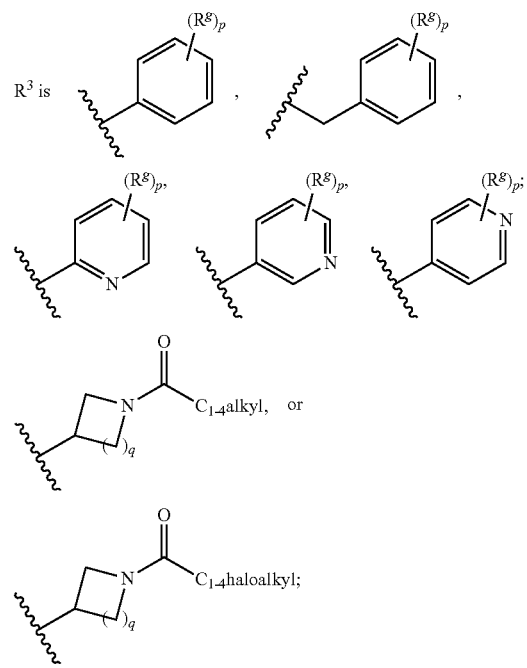

$R^g$ is halogen, $C_{1-4}$alkyl, $C_{1-4}$haloalkyl, —O—$C_{1-4}$ alkyl, OH, or —NHC(O)$C_{1-4}$alkyl; p is 1-3; and q is 1-4. Further exemplary $R^3$ is include

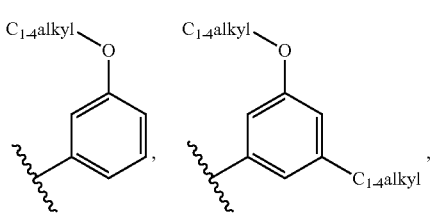

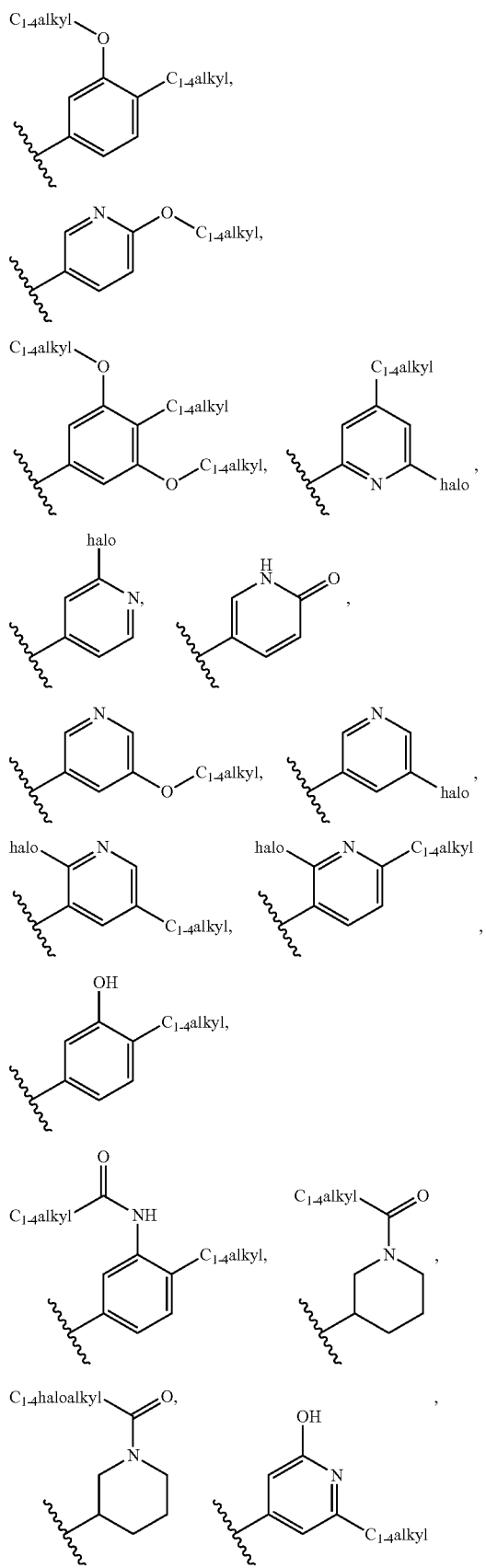
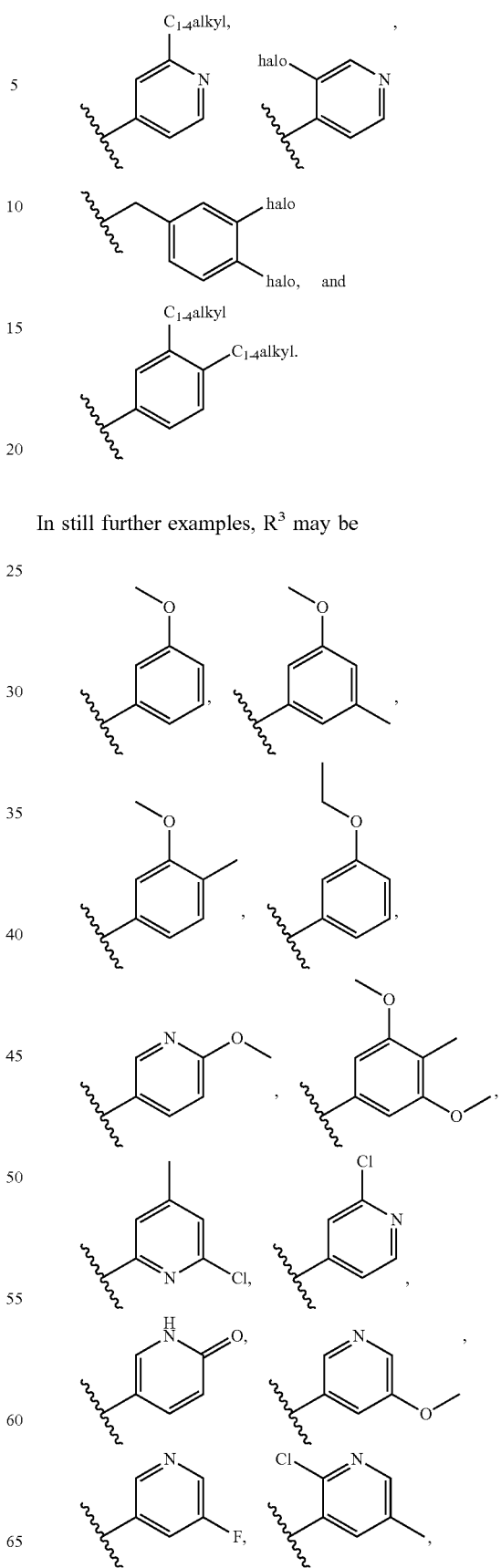
In still further examples, $R^3$ may be

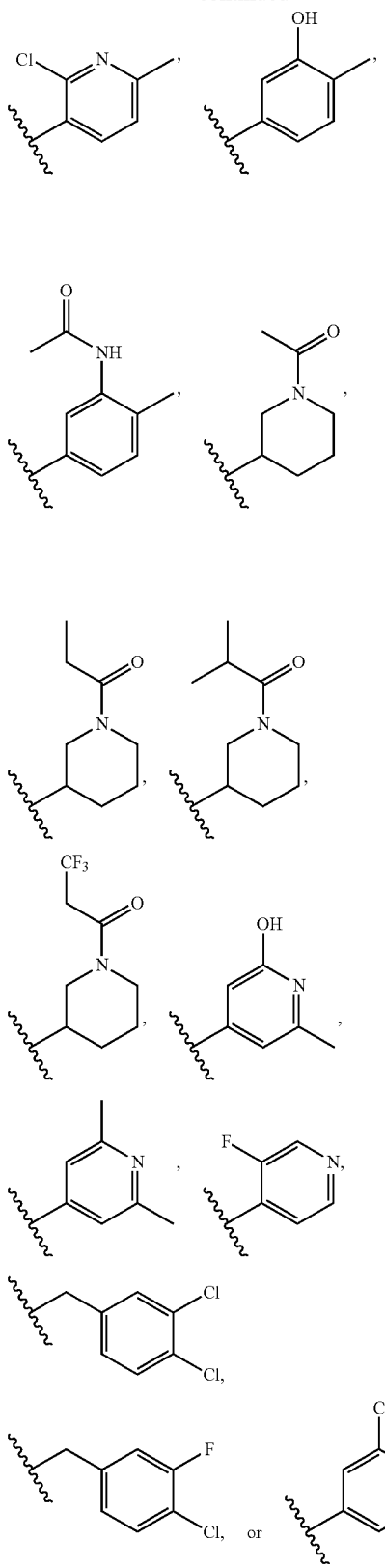

In some embodiments, the compounds of formula (I) have the stereochemistry as shown in formula (I-a).

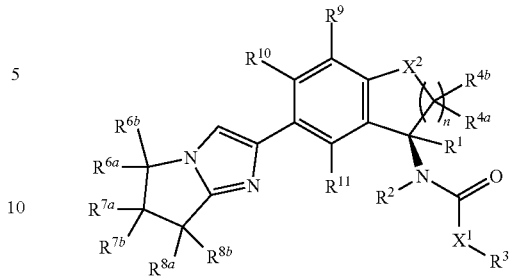

In some embodiments, compounds have formula (I) or (I-a), wherein $R^1$ is hydrogen; $R^2$ is hydrogen or $C_{3-8}$cycloalkyl-$C_{1-3}$alkylene-; $X^1$ is a bond; $R^3$ is $G^1$ or -$L^1$-$G^2$; $G^1$ and $G^2$ are a 4- to 8-membered heterocyclyl, aryl, or heteroaryl, wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl; $L^1$ is —$C_{1-3}$alkylene-; $R^{4a}$, at each occurrence, is hydrogen; $R^{4b}$, at each occurrence, is hydrogen; n is 1 or 2; $X^2$ is $C(R^{4a})(R^{4b})$ or $N(R^5)$; $R^5$ is —C(O)$C_{1-4}$alkyl; and $R^{6a}R^{6b}$, $R^{7a}$, $R^{7b}$, $R^{8a}$, $R^{8b}$, $R^9$, $R^{10}$, and $R^{11}$ are each hydrogen.

In some embodiments, the compound of formula (I) is selected from the group consisting of:

N-(cyclopropylmethyl)-N-(6-(6,7-dihydro-5H-pyrrolo[1,2-a]imidazol-2-yl)-2,3-dihydro-1H-inden-1-yl)-3-methoxybenzamide;

N-(6-(6,7-dihydro-5H-pyrrolo[1,2-a]imidazol-2-yl)-2,3-dihydro-1H-inden-1-yl)-4-methyl-3-(trifluoromethyl)benzamide;

N-(6-(6,7-dihydro-5H-pyrrolo[1,2-a]imidazol-2-yl)-2,3-dihydro-1H-inden-1-yl)-3-methoxy-4-methylbenzamide;

N-(6-(6,7-dihydro-5H-pyrrolo[1,2-a]imidazol-2-yl)-2,3-dihydro-1H-inden-1-yl)-3-ethoxybenzamide;

N-(6-(6,7-dihydro-5H-pyrrolo[1,2-a]imidazol-2-yl)-2,3-dihydro-1H-inden-1-yl)-3-methoxy-5-methylbenzamide;

2-(3,4-dichlorophenyl)-N-(6-(6,7-dihydro-5H-pyrrolo[1,2-a]imidazol-2-yl)-2,3-dihydro-1H-inden-1-yl)acetamide;

1-acetyl-N-(6-(6,7-dihydro-5H-pyrrolo[1,2-a]imidazol-2-yl)-2,3-dihydro-1H-inden-1-yl)piperidine-3-carboxamide;

N-(6-(6,7-dihydro-5H-pyrrolo[1,2-a]imidazol-2-yl)-2,3-dihydro-1H-inden-1-yl)-1-propionylpiperidine-3-carboxamide;

N-(6-(6,7-dihydro-5H-pyrrolo[1,2-a]imidazol-2-yl)-2,3-dihydro-1H-inden-1-yl)-1-(3,3,3-trifluoropropanoyl)piperidine-3-carboxamide;

N-(6-(6,7-dihydro-5H-pyrrolo[1,2-a]imidazol-2-yl)-2,3-dihydro-1H-inden-1-yl)-1-isobutyrylpiperidine-3-carboxamide;

(R)-2-(3,4-dichlorophenyl)-N-(6-(6,7-dihydro-5H-pyrrolo[1,2-a]imidazol-2-yl)-2,3-dihydro-1H-inden-1-yl)acetamide;

(R)—N-(6-(6,7-dihydro-5H-pyrrolo[1,2-a]imidazol-2-yl)-2,3-dihydro-1H-inden-1-yl)-3-methoxy-4-methylbenzamide;

1-acetyl-N—((R)-6-(6,7-dihydro-5H-pyrrolo[1,2-a]imidazol-2-yl)-2,3-dihydro-1H-inden-1-yl)piperidine-3-carboxamide;

(R)—N-(7-(6,7-dihydro-5H-pyrrolo[1,2-a]imidazol-2-yl)-1,2,3,4-tetrahydronaphthalen-1-yl)-3-methoxy-4-methylbenzamide;

(R)-2-(4-chloro-3-fluorophenyl)-N-(6-(6,7-dihydro-5H-pyrrolo[1,2-a]imidazol-2-yl)-2,3-dihydro-1H-inden-1-yl)acetamide;

N—((R)-6-(6,7-dihydro-5H-pyrrolo[1,2-a]imidazol-2-yl)-2,3-dihydro-1H-inden-1-yl)-1-propionylpiperidine-3-carboxamide;

1-acetyl-N—((R)-7-(6,7-dihydro-5H-pyrrolo[1,2-a]imidazol-2-yl)-1,2,3,4-tetrahydronaphthalen-1-yl)piperidine-3-carboxamide;

N—((R)-7-(6,7-dihydro-5H-pyrrolo[1,2-a]imidazol-2-yl)-1,2,3,4-tetrahydronaphthalen-1-yl)-1-propionylpiperidine-3-carboxamide;

(R)—N-(6-(6,7-dihydro-5H-pyrrolo[1,2-a]imidazol-2-yl)-2,3-dihydro-1H-inden-1-yl)-6-methoxynicotinamide;

(R)-2-chloro-N-(6-(6,7-dihydro-5H-pyrrolo[1,2-a]imidazol-2-yl)-2,3-dihydro-1H-inden-1-yl)isonicotinamide;

(R)-2-chloro-N-(6-(6,7-dihydro-5H-pyrrolo[1,2-a]imidazol-2-yl)-2,3-dihydro-1H-inden-1-yl)-5-methylnicotinamide;

(R)—N-(6-(6,7-dihydro-5H-pyrrolo[1,2-a]imidazol-2-yl)-2,3-dihydro-1H-inden-1-yl)-6-methyl-2-oxo-1,2-dihydropyridine-4-carboxamide;

(R)-6-chloro-N-(6-(6,7-dihydro-5H-pyrrolo[1,2-a]imidazol-2-yl)-2,3-dihydro-1H-inden-1-yl)-4-methylpicolinamide;

(R)—N-(6-(6,7-dihydro-5H-pyrrolo[1,2-a]imidazol-2-yl)-2,3-dihydro-1H-inden-1-yl)-2-methylisonicotinamide;

(R)—N-(6-(6,7-dihydro-5H-pyrrolo[1,2-a]imidazol-2-yl)-2,3-dihydro-1H-inden-1-yl)-3-hydroxy-4-methylbenzamide;

(R)—N-(6-(6,7-dihydro-5H-pyrrolo[1,2-a]imidazol-2-yl)-2,3-dihydro-1H-inden-1-yl)-5-methoxynicotinamide;

(R)-3-acetamido-N-(6-(6,7-dihydro-5H-pyrrolo[1,2-a]imidazol-2-yl)-2,3-dihydro-1H-inden-1-yl)-4-methylbenzamide;

(R)-2-chloro-N-(6-(6,7-dihydro-5H-pyrrolo[1,2-a]imidazol-2-yl)-2,3-dihydro-1H-inden-1-yl)-6-methylnicotinamide;

(R)—N-(6-(6,7-dihydro-5H-pyrrolo[1,2-a]imidazol-2-yl)-2,3-dihydro-1H-inden-1-yl)-3,5-dimethoxy-4-methylbenzamide;

(R)—N-(6-(6,7-dihydro-5H-pyrrolo[1,2-a]imidazol-2-yl)-2,3-dihydro-1H-inden-1-yl)-3-fluoroisonicotinamide;

(R)—N-(6-(6,7-dihydro-5H-pyrrolo[1,2-a]imidazol-2-yl)-2,3-dihydro-1H-inden-1-yl)-6-oxo-1,6-dihydropyridine-3-carboxamide;

(R)—N-(6-(6,7-dihydro-5H-pyrrolo[1,2-a]imidazol-2-yl)-2,3-dihydro-1H-inden-1-yl)-5-fluoronicotinamide; and (R)—N-(1-acetyl-6-(6,7-dihydro-5H-pyrrolo[1,2-a]imidazol-2-yl)-1,2,3,4-tetrahydroquinolin-4-yl)-3-methoxy-4-methylbenzamide, or a pharmaceutically acceptable salt thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. BINDING TO WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 µM. The compounds may have a $K_i$ of about 250 µM, about 200 µM, about 150 µM, about 100 µM, about 90 µM, about 80 µM, about 70 µM, about 60 µM, about 50 M, about 40 µM, about 30 µM, about 20 µM, about 10 µM, about 9 µM, about 8 µM, about 7 M, about 6 µM, about 5 µM, about 4 µM, about 3 µM, about 2 µM, about 1 µM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 µM, less than 200 µM, less than 150 µM, less than 100 µM, less than 90 µM, less than 80 M, less than 70 µM, less than 60 µM, less than 50 µM, less than 40 µM, less than 30 µM, less than 20 µM, less than 10 µM, less than 9 µM, less than 8 µM, less than 7 µM, less than 6 µM, less than 5 µM, less than 4 µM, less than 3 µM, less than 2 µM, less than 1 µM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. GENERAL SYNTHESIS

Compounds of formula (I) may be prepared by synthetic processes or by metabolic processes. Preparation of the compounds by metabolic processes includes those occurring in the human or animal body (in vivo) or processes occurring in vitro.

Several methods for preparing the compounds of this invention are illustrated in the Schemes and Examples herein. Starting materials are made according to procedures known in the art or as illustrated herein. The following examples are provided so that the invention might be more fully understood and illustrate details for the preparation of the compounds of the present invention. These examples are illustrative only and should not be construed as limiting the invention in any way.

In one approach, example compounds may be prepared according to Scheme 1. Starting from 2-bromo-6,7-dihydro-5H-pyrrolo[1,2-a]imidazole 1.1, Suzuki cross-coupling using an appropriate bicyclic boronic acid or ester 1.2, gives ketone precursor 1.3. Condensation with either racemic or preselected chiral R or S Ellman 2-methyl-2-propanesulfinamide (Robak, M. T., Herbage, M. A., Ellman, J. A. Chem. Rev., 2010, 110, 3600-3740) in the presence of titanium tetraethoxide in THF provides the sulfinimine intermediate. Within the same pot the imine adduct is treated with a reductant, such as sodium borohydride, to afford after workup and purification the desired amine 1.4. Deprotection of the Ellman auxiliary using acid gives penultimate amine salt 1.5. Amide coupling gives examples of type 1.6. Optional alkylation using alkylating agents, for example (bromomethyl)cyclopropane, in the presence of base, such as sodium hydride, in a polar aprotic solvent, such as DMF, may be performed to afford final compounds of type 1.7.

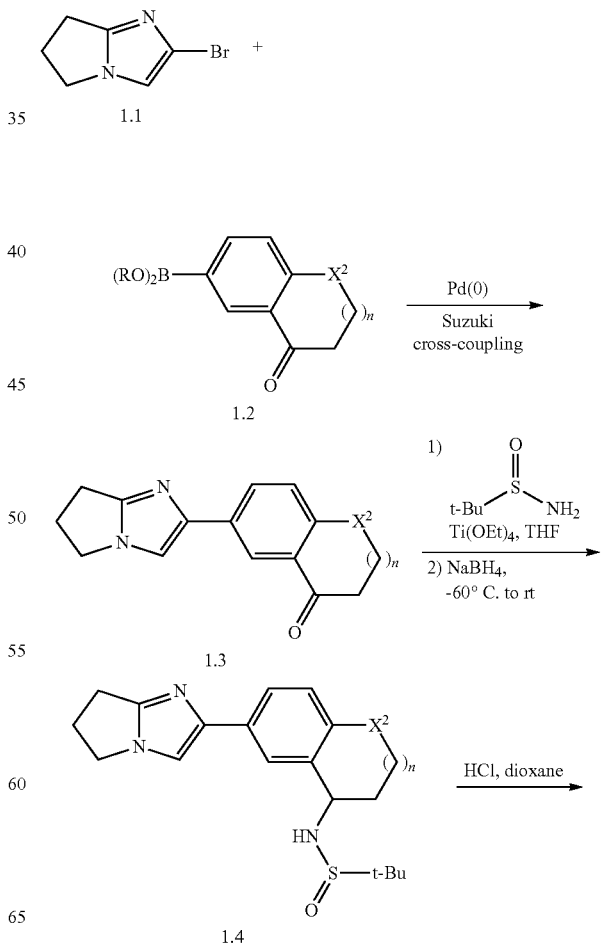

SCHEME 1

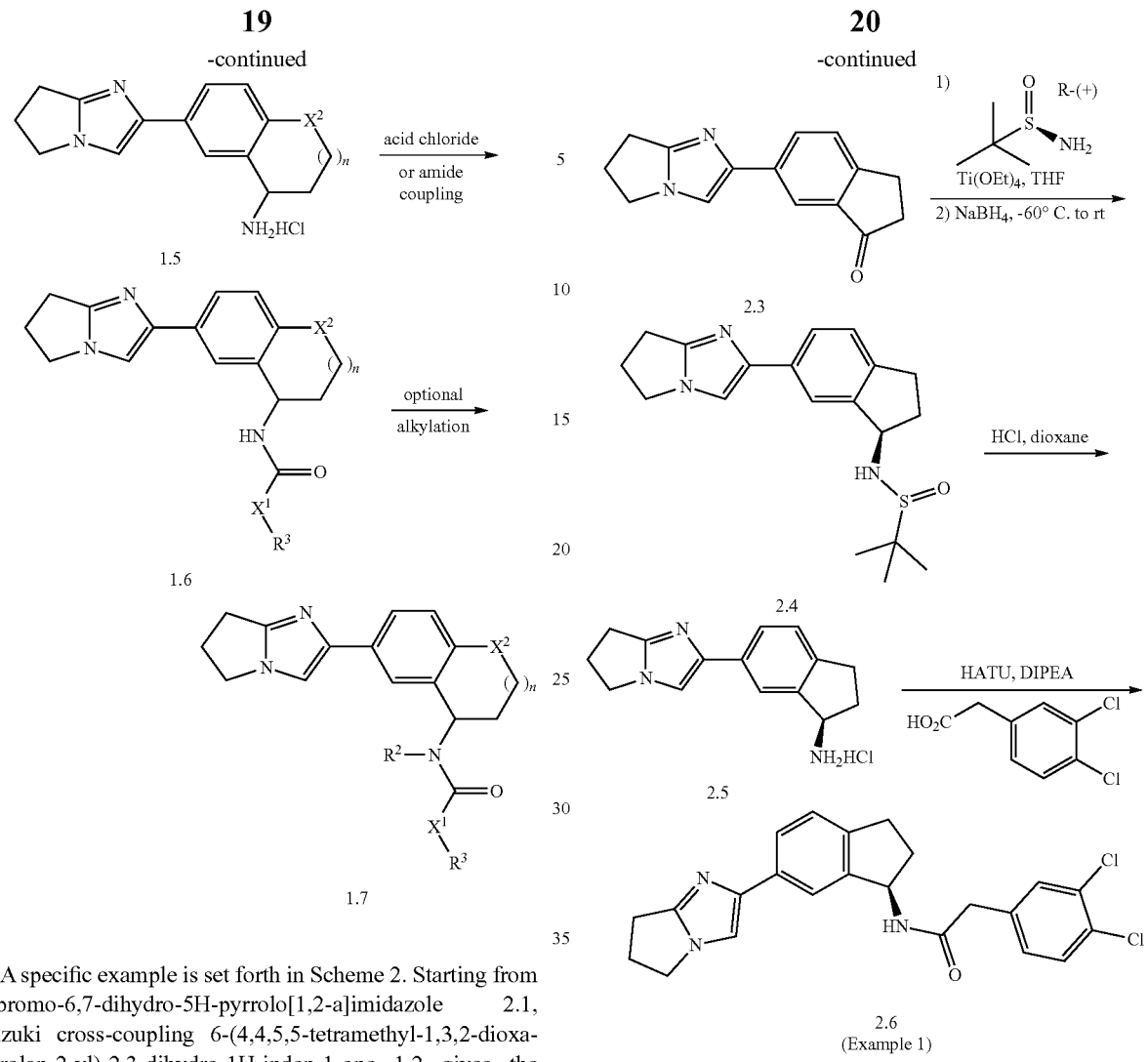

A specific example is set forth in Scheme 2. Starting from 2-bromo-6,7-dihydro-5H-pyrrolo[1,2-a]imidazole 2.1, Suzuki cross-coupling 6-(4,4,5,5-tetramethyl-1,3,2-dioxa-borolan-2-yl)-2,3-dihydro-1H-inden-1-one 1.2 gives the required indanone precursor 2.3. Condensation with Ellman (R)-(+)-2-methyl-2-propanesulfinamide in the presence of titanium tetraethoxide in THF provides the imine intermediate. Reduction with sodium borohydride proceeds to afford the favoured diastereomer 2.4 containing R-configuration at the benzylic position. Deprotection of the Ellman auxiliary gives penultimate amine 2.5. Final amide coupling 3,4-dichlorophenyl acetic acid in the presence of HATU and DIPEA gives 2.6 (see Example 1).

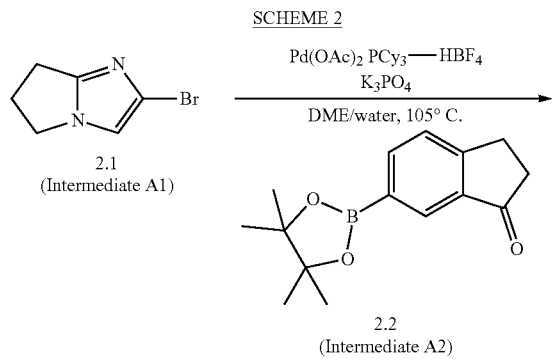

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. EXAMPLES

Definitions: the term "EtOAc" means ethyl acetate, "DCM" means dichloromethane, "DIPEA" means N,N-diisopropylethylamine, "DMF" means N,N-dimethylformamide, "DTBAD" means di-tert-butyl azodicarboxylate, "HATU" means 2-(7-aza-1H-benzotriazole-1-yl)-1,1,3,3-tetramethyluronium hexafluorophosphate, "LC-MS" means liquid chromatography/mass spectrometry, "MeOH" means methanol, "[M+H]+" means the protonated mass of the free base of the compound, "M. p." means melting point, "NMR" means nuclear magnetic resonance, "$R_t$" means retention time (in minutes), "THF" means tetrahydrofuran.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc. or using a Parr hydrogenation shaker apparatus.

Analytical thin layer chromatography is performed on Analtech silica gel GF 250 micron plates using reagent grade solvents.

Normal phase flash silica gel-based column chromatography is performed using ready-to-connect cartridges from ISCO, on irregular silica gel, particle size 15-40 m on a Combi-flash Companion chromatography system from ISCO.

Low resolution mass spectra were obtained on an Agilent 1200 series 6130 mass spectrometer. High resolution mass spectra were recorded on a Waters Q-TOF API-US. Analytical HPLC was performed on an HP 1100 with UV detection at 214 and 254 nm along with ELSD detection, LC/MS (J-Sphere80-C18, 3.0×50 mm, 4.1 min gradient, 5%[0.05% TFA/CH$_3$CN]:95%[0.05% TFA/H$_2$O] to 100% [0.05% TFA/CH$_3$CN]. Preparative RP-HPLC purification was performed on a custom HPi1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

For LC-MS-characterization of the compounds of the present invention, the following methods were used.

Method 1:

The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software. Reversed phase HPLC was carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Method 2:

Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Chiral purification of racemic mixtures was accomplished using a supercritical fluid chromatography (SFC) instrument

Preparation of Intermediates

Intermediate A1. 2-Bromo-6,7-dihydro-5H-pyrrolo[1,2-a]imidazole

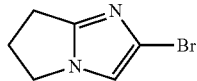

Phosphorus(V) oxybromide (6.05 g, 21.1 mmol) was added to piracetam (1.50 g, 10.6 mmol) at room temperature. The reaction mixture was stirred at 85° C. for 30 min. The reaction was diluted with DCM and ice. $K_2CO_3$ (solid) was added slowly and extracted with DCM (3×20 mL). The combined organic layer was dried (MgSO4), filtered and concentrated. The residue was purified on ISCO (20% MeOH in DCM) to provide the desired product as a white solid (1.30 g, 66% yield): $^1$H NMR (400 MHz, MeOH-d4) δ 7.05 (s, 1H), 4.02 (t, J=7.2, 2H), 2.83 (t, J=7.2, 2H), 2.58 (pent, J=7.5, 2H); LC-MS, >98% (215, 254 nm), $R_f$=0.090, m/z=187.1 [M+H].

Intermediate A2. 6-(4,4,5,5-Tetramethyl-1,3,2-dioxaborolan-2-yl)-2,3-dihydro-1H-inden-1-one

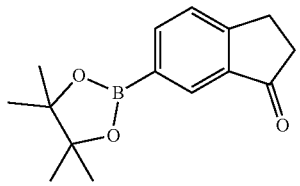 [SMILES: CC1(C)OB(c2ccc3c(c2)C(=O)CC3)OC1(C)C]

6-Bromo-2,3-dihydro-1H-inden-1-one (2.0 g, 9.5 mmol), bis(pinacolato)diborane (3.1 g, 12.3 mmol), $PdCl_2(dppf) \cdot CH_2Cl_2$ (390 mg, 0.47 mmol) and potassium acetate (2.8 g, 28 mmol) were taken in toluene (40 mL) under an inert atmosphere and heated to 90° C. for 12 h. The cooled mixture was diluted with EtOAc and filtered through Celite, washing with further EtOAc. The filtrate was washed with water, sat. aq. NaCl and concentrated under reduced pressure. Purification by flash column chromatography (80 g silica, 0-20% EtOAc in hexanes) afforded a pale yellow solid (2.35 g, 9.10 mmol, 96%): $^1$H NMR (400 MHz, DMSO-d6) δ 7.91 (d, 1H, J=7.5), 7.89 (s, 1H), 7.60 (d, 1H, J=7.5), 3.14-3.11 (m, 2H), 2.66-2.62 (m, 2H), 1.21 (s, 12H); LC-MS >95% (215, 254 nm).

Preparation of Representative Compounds

Example 1 (Table 1, B11)

(R)-2-(3,4-dichlorophenyl)-N-(6-(6,7-dihydro-5H-pyrrolo[1,2-a]imidazol-2-yl)-2,3-dihydro-1H-inden-1-yl)acetamide

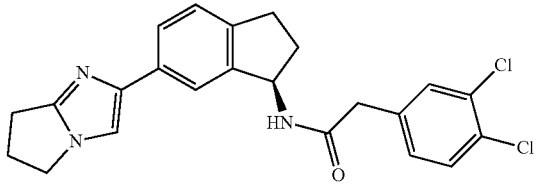 [SMILES: O=C(Cc1ccc(Cl)c(Cl)c1)N[C@@H]1CCc2ccc(-c3cn4c(n3)CCC4)cc21]

Suzuki Coupling Step:

Intermediate A2 6-(4,4,5,5-tetramethyl-1,3,2-dioxaborolan-2-yl)-2,3-dihydro-1H-inden-1-one (100 mg, 0.53 mmol), intermediate A1 2-bromo-6,7-dihydro-5H-pyrrolo[1,2-a]imidazole (221 mg, 0.86 mmol), $Pd(OAc)_2$ (12 mg, 0.05 mmol), PCy3.HBF4 (30 mg, 0.08 mmol) and $K_3PO_4$ (230 mg, 1.1 mmol) were combined and taken under an inert atmosphere. DME:water (4 mL, 5:1) was added and the mixture heated to 105° C. for 16 h. The cooled mixture was diluted with EtOAc, filtered through Celite, washed further with EtOAc and the filtrate concentrated under reduced pressure. Purification by flash column chromatography (12 g $SiO_2$, gradient 0-5% MeOH in DCM, with 1% (w/w) $NH_4OH$ in a 20% MeOH/DCM solution) afforded 6-(6,7-dihydro-5H-pyrrolo[1,2-a]imidazol-2-yl)-2,3-dihydro-1H-inden-1-one as off-white solid (60 mg, 47%): $^1$H NMR (DMSO-d6) δ 8.03 (dd, 1H, J=8.0, 1.7), 7.92 (d, 1H, J=1.7), 7.67 (s, 1H), 7.53 (d, 1H, J=8.0), 3.97 (t, 2H, J=7.0), 3.09-3.06 (m, 2H), 2.76 (t, 2H, J=7.0), 2.66-2.62 (m, 2H), 2.55-2.49 (m, 2H); LC-MS >95% (215, 254 nm).

Auxiliary Condensation and Reduction Step:

6-(6,7-Dihydro-5H-pyrrolo[1,2-a]imidazol-2-yl)-2,3-dihydro-1H-inden-1-one (410 mg, 1.72 mmol) and (R)-(+)-2-methyl-2-propanesulfinamide (417 mg, 3.44 mmol) were dissolved in THF (3.4 mL) under an inert atmosphere. $Ti(OEt)_4$ (1.44 mL, 6.9 mmol) was added and the mixture heated to reflux for 18 h. To the cooled slurry was added further THF (2 mL), aiding dissolution. The mixture was cooled to −60° C. (dry ice/IPA) and $NaBH_4$ (262 mg, 6.9 mmol) was added portion-wise and stirred for 0.5 h, then warmed to 0° C. and quenched by the drop-wise addition of MeOH until gas evolution ceased. The resulting slurry was filtered, washed with EtOAc, and brine added to the eluent and stirred vigorously for 1 h. The aqueous layer was separated and extracted with EtOAc (2×). The combined organic layers were dried ($MgSO_4$) and concentrated under reduced pressure; purification by flash column chromatography (40 g $SiO_2$, gradient 0-2.5% MeOH in DCM, with 1% (w/w) $NH_4OH$ in a 20% MeOH/$CH_2Cl_2$ solution) afforded N—((R)-6-(6,7-dihydro-5H-pyrrolo[1,2-a]imidazol-2-yl)-2,3-dihydro-1H-inden-1-yl)-2,2-dimethyl-2-propane-2-sulfinamide as a pale yellow solid (368 mg, 1.07 mmol, 62%): $^1$H NMR ($CD_3OD$) δ 7.77 (s, 1H), 7.68 (d, 1H, J=8.0), 7.26-7.23 (m, 2H), 4.15 (t, 2H, J=7.2), 3.05 (t, 2H, J=7.2), 3.03-2.99 (m, 1H), 2.90-2.80 (m, 1H), 2.65 (p, 7.2), 2.56-2.46 (m, 1H), 2.12-2.03 (m, 1H), 1.25 (s, 9H); LC-MS >95% (215, 254 nm).

Deprotection:

N—((R)-6-(6,7-Dihydro-5H-pyrrolo[1,2-a]imidazol-2-yl)-2,3-dihydro-1H-inden-1-yl)-2,2-dimethyl-2-propane-2-sulfinamide (140 mg, 0.41 mmol) was dissolved in MeOH (3 mL) and HCl ([4.0 M] in dioxane, 0.31 mL, 1.2 mmol) was added drop-wise at rt, and stirred for 1 h upon complete addition. The mixture was concentrated under reduced pressure and dried in a vacuum oven to afford crude (R)-6-(6,7-dihydro-5H-pyrrolo[1,2-a]imidazol-2-yl)-2,3-dihydro-1H-inden-1-amine hydrochloride as a pale yellow solid (110 mg, 97%) which was used without further purification: LCMS >90% (215, 254 nm), m/z=240.1 [M+H].

Amide Coupling Step:

(R)-6-(6,7-Dihydro-5H-pyrrolo[1,2-a]imidazol-2-yl)-2,3-dihydro-1H-inden-1-amine hydrochloride (45 mg, 0.19 mmol), 3,4-dichlorophenylacetic acid (42 mg, 0.21 mmol), HATU (0.23 mmol, 86 mg) and DIPEA (0.95 mmol, 123 mg) were combined in DMF and stirred at rt for 16 h. Upon complete conversion of starting material the mixture was diluted with EtOAc, washed sequentially with water, sat. aq. NaHCO$_3$, and sat. aq. NaCl. The organic phase was concentrated and the crude material purified by flash column chromatography (12 g SiO$_2$, 0-3.5% MeOH/CH$_2$Cl$_2$) to afford a tan solid (47 mg, 58%): $^1$H NMR (400 MHz, CD$_3$OD) δ 7.56-7.52 (m, 2H), 4.48 (d, 1H, J=7.4), 7.41 (s, 1H), 7.28 (d, 1H, J=7.4), 7.23-7.19 (m, 2H), 5.37 (t, 1H, J=7.5), 4.05 (t, 2H, J=7.0), 3.55 (d, 2H, J=4.2), 3.02-2.94 (m, 1H), 2.87 (t, 2H, J=7.0), 2.84-2.80 (m, 1H), 2.63 (dt, 2H, J=7.0, 7.0), 2.56-2.47 (m, 1H), 1.93-1.81 (m, 1H); LCMS >95% (215, 254 nm), R$_t$=1.04 min, m/z=418.1 [M+H].

Characterization of Exemplary Compounds

The compounds of formula I below in Table 1 were synthesized with methods identical or analogous to those described herein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H] means the protonated mass of the free base of the compound.

| No. | Compound | LC-MS [M + H] | Retention time |
|---|---|---|---|
| B1 | | 428.2 | 0.84 |
| B2 | | 426.2 | 0.95 |
| B3 | | 388.2 | 0.86 |

-continued
| No. | Compound | LC-MS [M + H] | Retention time |
|---|---|---|---|
| B4 | 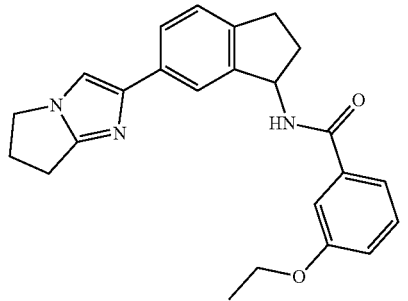 [SMILES: CCOc1cccc(C(=O)NC2CCc3ccc(-c4cn5c(n4)CCC5)cc32)c1] | 388.2 | 0.87 |
| B5 | 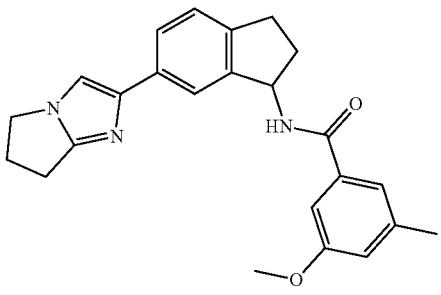 [SMILES: COc1cc(C)cc(C(=O)NC2CCc3ccc(-c4cn5c(n4)CCC5)cc32)c1] | 388.2 | 0.88 |
| B6 | 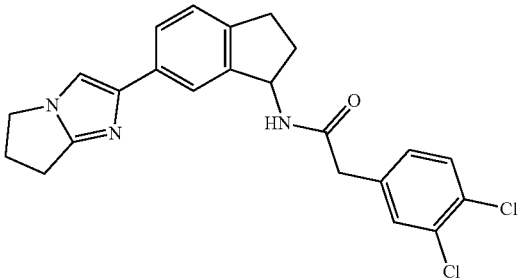 [SMILES: O=C(Cc1ccc(Cl)c(Cl)c1)NC1CCc2ccc(-c3cn4c(n3)CCC4)cc21] | 426.1 | 0.90 |
| B7 | 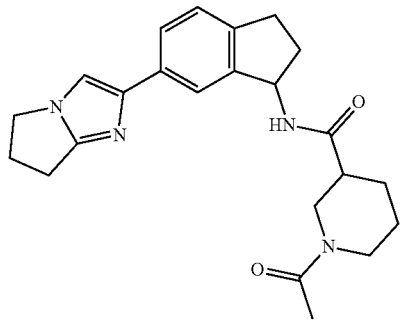 [SMILES: CC(=O)N1CCCC(C(=O)NC2CCc3ccc(-c4cn5c(n4)CCC5)cc32)C1] | 393.2 | 0.91 |
| B8 | 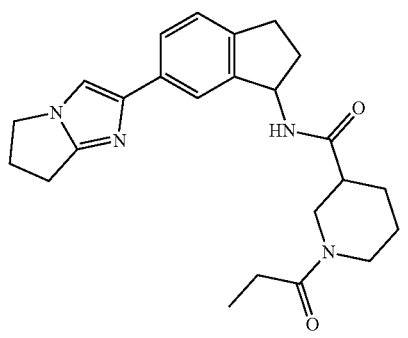 [SMILES: CCC(=O)N1CCCC(C(=O)NC2CCc3ccc(-c4cn5c(n4)CCC5)cc32)C1] | 407.2 | 0.95 |

-continued
| No. | Compound | LC-MS [M + H] | Retention time |
|---|---|---|---|
| B9 | 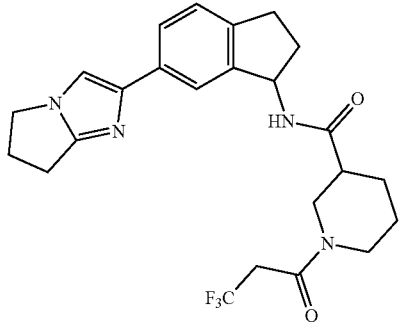 [SMILES: O=C(NC1CCc2ccc(-c3cn4c(n3)CCC4)cc21)C1CCCN(C(=O)CC(F)(F)F)C1] | 461.2 | 1.05 |
| B10 | 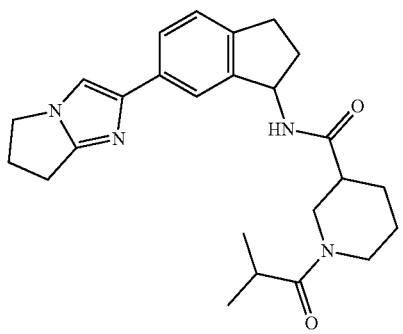 [SMILES: CC(C)C(=O)N1CCCC(C(=O)NC2CCc3ccc(-c4cn5c(n4)CCC5)cc32)C1] | 421.3 | 1.06 |
| B11 | 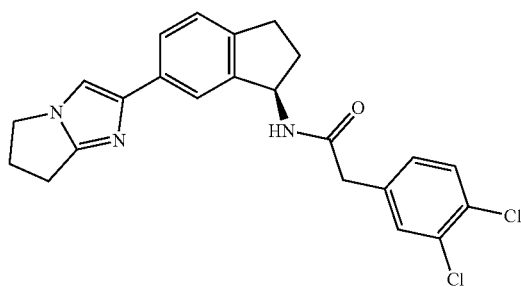 | 426.1 | 0.90 |
[Example 1]
| | | | |
|---|---|---|---|
| B12 | 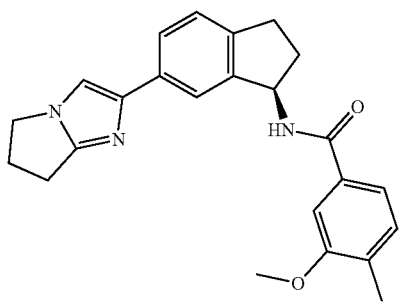 [SMILES: COc1cc(C(=O)N[C@@H]2CCc3ccc(-c4cn5c(n4)CCC5)cc32)ccc1C] | 388.2 | 0.90 |

-continued

| No. | Compound | LC-MS [M + H] | Retention time |
|---|---|---|---|
| B13 | | 393.2 | 0.70 |
| B14 | | 402.2 | 0.90 |
| B15 | | 410.1 | 0.85 |
| B16 | | 407.2 | 0.68 |

-continued
| No. | Compound | LC-MS [M + H] | Retention time |
|---|---|---|---|
| B17 | 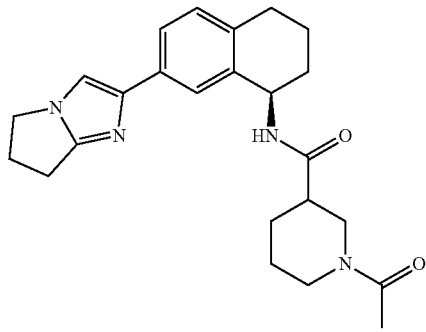 [SMILES: CC(=O)N1CCCC(C(=O)N[C@@H]2CCCc3ccc(-c4cn5c(n4)CCC5)cc32)C1] | 407.2 | 0.72 |
| B18 | 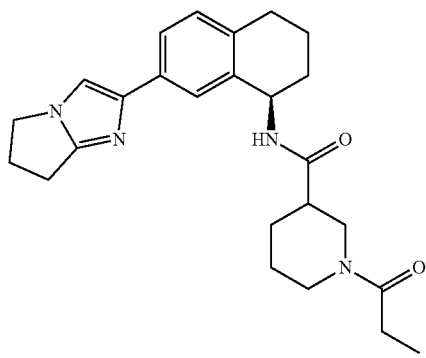 [SMILES: CCC(=O)N1CCCC(C(=O)N[C@@H]2CCCc3ccc(-c4cn5c(n4)CCC5)cc32)C1] | 421.3 | 0.75 |
| B19 | 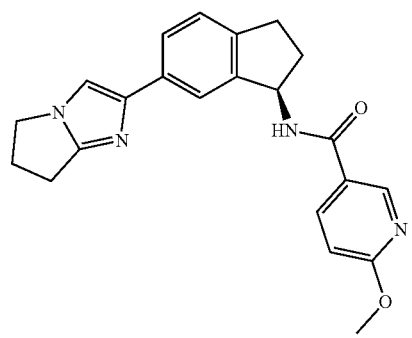 [SMILES: COc1ccc(C(=O)N[C@@H]2CCc3ccc(-c4cn5c(n4)CCC5)cc32)cn1] | 375.2 | 0.73 |
| B20 | 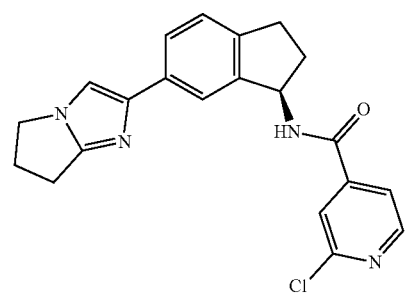 [SMILES: O=C(N[C@@H]1CCc2ccc(-c3cn4c(n3)CCC4)cc21)c1ccnc(Cl)c1] | 379.1 | 0.74 |

-continued

| No. | Compound | LC-MS [M + H] | Retention time |
|---|---|---|---|
| B21 | | 393.1 | 0.76 |
| B22 | | 375.2 | 0.71 |
| B23 | | 393.1 | 0.88 |
| B24 | | 359.2 | 0.64 |
| B25 | | 374.2 | 0.81 |

-continued
| No. | Compound | LC-MS [M + H] | Retention time |
|---|---|---|---|
| B26 | 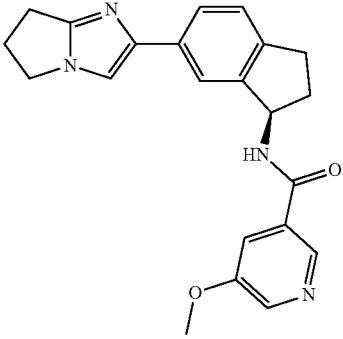 [SMILES: COc1cncc(C(=O)N[C@@H]2CCc3ccc(-c4cn5c(n4)CCC5)cc32)c1] | 375.2 | 0.70 |
| B27 | 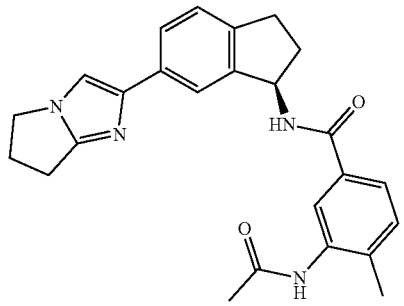 [SMILES: CC(=O)Nc1cc(C(=O)N[C@@H]2CCc3ccc(-c4cn5c(n4)CCC5)cc32)ccc1C] | 415.2 | 0.75 |
| B28 | 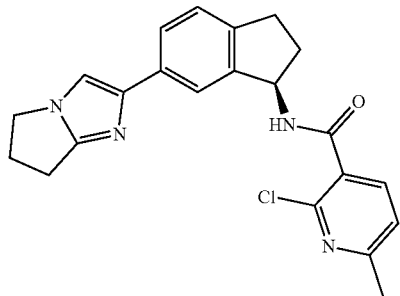 [SMILES: Cc1ccc(C(=O)N[C@@H]2CCc3ccc(-c4cn5c(n4)CCC5)cc32)c(Cl)n1] | 393.1 | 0.76 |
| B29 | 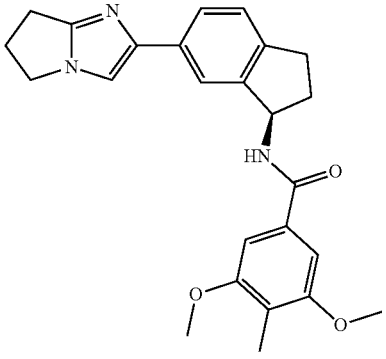 [SMILES: COc1cc(C(=O)N[C@@H]2CCc3ccc(-c4cn5c(n4)CCC5)cc32)cc(OC)c1C] | 418.2 | 0.94 |

| No. | Compound | LC-MS [M + H] | Retention time |
|---|---|---|---|
| B30 | | 363.2 | 0.76 |
| B31 | | 361.2 | 0.69 |
| B32 | | 363.2 | 0.74 |
| B33 | | 445.2 | 1.10 |

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila* trithorax (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result in-frame fusion of 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, γ-radiation, DOT1L inhibitors, agents targeting epigenetic mechanisms, or an additional chemotherapeutic agent such as N-Ac-Sar-Gly-Val-D-allole-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl}-N'-(2-fluoro-5-methylphenyl)urea or a salt thereof, N-(4-(4-aminothieno[2,3-d]pyrimidin-5-yl)phenyl}-N'-(2-fluoro-5-(trifluoromethyl)phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB 1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

A fluorescence polarization anisotropy (FPA) assay that measures the displacement of either a FITC-labeled MLL-derived peptide or a more potent 10mer-Thr-FAM probe in response to compound treatment is performed (Karatas et al. J. Med. Chem. 2010, 5179.). The assay is run in 384-well format and is read on a BioTek Cytation. Compounds are run as 2 replicates on the left and right sides of the plate; therefore a plate can accommodate 16 compounds in a 10-point, 3-fold dilution scheme, plus positive and negative controls. Replicate values are fit to a 4-parameter fit in XLFit to generate a single $IC_{50}$ value for each compound that is then converted to a $K_i$ value. Experiments are repeated to generate a $2^{nd}$, independent $K_i$ value; values from the two experiments are averaged to produce the reported $K_i$ value for the compound. The assay performs with an average Z' value of 0.7, and is tolerant of up to 5% DMSO.

FPA Assay protocol adopted from Karatas et al. (J. Med. Chem. 2010, 5179.; J. Amer. Chem. Soc. 2013, 669.): WDR5 (Δ23, residues 24-334), is expressed and purified in sufficient quantities for screening. FITC-MLL peptide (FITC-GSARAEVHLRKS) and 10mer-Thr-FAM (ARTE-VHLRKS-(Ahx-Ahx)(Lys-(5-FAM))) were purchased from GeneScript and used without additional purification. FITC-MLL peptide is used at 50 nM, while WDR5 is added at the $K_i$ value of the protein:peptide interaction (WDR5-WIN $K_i$=2.5 µM). 10mer-Thr-FAM peptide is used at 4 nM, while WDR5 is added at the $K_i$ value of the protein:peptide interaction (WDR5-10mer-Thr $K_i$=4 nM).

Stock compounds are dispensed in barcoded 384-well plates as 30 mM solutions in DMSO. This plate is used as the source plate for the Echo Liquid Handler, which distributes the compounds to the assay plate (black, flat-bottom; Greiner) in a 10-point, 3-fold dilution scheme with a top concentration of 100 µM (5 nM low concentration) in a final volume of 50 µL. Both the top concentration and the dilution scheme can be adjusted to fit the anticipated potency of the compounds.

For the FITC-MLL assay, 2.5 µM WDR5 and 50 nM FITC-MLL peptide in assay buffer (1× Phosphate Buffered Saline, pH 6.0, 300 mM NaCl, 0.5 mM TCEP, 0.1% CHAPS) is added to all compound-containing wells and to columns 2, 24 (negative control, 0% inhibition). 2 µL of 50 nM FITC-MLL peptide alone in assay buffer is added to columns 1, 23 (positive control, 100% inhibition). For the 10mer-Thr-FAM assay, a similar addition protocol is performed, using 4 nM WDR5 and 4 nM 10mer-Thr-FAM peptide in assay buffer (1× Phosphate Buffered Saline pH 6.0, 300 mM NaCl, 0.5 mM TCEP, 0.1% CHAPS).

The plate is covered, shielded from light, and incubated for 60 min at room temperature, with rocking. Anisotropy is measured on the BioTek Cytation at an excitation wavelength of 480 nm, and emission of 535 nm. Total fluorescence is also measured, to rule out compounds that are inherently fluorescent or able to act as quenchers in the assay.

A Time-Resolved Fluorescence Resonance Energy Transfer (TR-FRET) assay that measures the displacement of the 10mer-Thr-FAM probe in response to compound treatment was performed for compounds wherein the $IC_{50}$ from FPA assay using 10mer-Thr-FAM was below the lower assay $IC_{50}$ limit ~1 nM. Excess 10mer-Thr-FAM probe was utilized with His-tagged WDR5 in conjunction with a commercial anti-His antibody containing a Terbium label. The LanthaScreen™ Elite Tb-anti-HIS Antibody from Thermo-Fisher Scientific was used for this purpose. This Tb-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an $IC_{50}$ value. By virtue of FRET there is little to no background fluorescence interference from 10mer-Thr-FAM probe allowing an excess of the probe to be used permitting an increase in the lower limit of the calculated $K_i$ when testing against highly potent inhibitors with $K_i \ll 1$ nM. WDR5-His Tag (Δ23, residues 24-334) is expressed and purified in our lab in sufficient quantities for screening. 10mer-Thr-FAM peptide is used anywhere from 15 to 150 nM depending on the window of sensitivity required. WDR5-His tag protein is used at 2 nM. A source plate is prepared using an Echo Liquid Handler, which distributes the compounds to the assay plate (white, flat-bottom; OptiPlate) in a 10-point, 3-fold dilution schemes with a top concentration of either 5 or 20 μM depending on the anticipated potency of the compounds, in a final volume of 20 μL. A final target (WDR5)/Tb-Ab concentration of 2 nM/1 nM is dispensed from appropriate stock solutions, respectively. The final DMSO concentration in each well of the assay plate is 1% or lower. As before the plate is covered, shielded from light, and incubated for 60 minutes at room temperature with rocking. Anisotropy is then measured on a Biotek Cytation 3 at excitation wavelength of 340 nm, and emission wavelengths of 495 nm and 520 nm. Working buffer conditions are similar to that in FPA above.

Data Analysis:

Anisotropy values are imported into a template in XLFit that uses a four-parameter fit to generate an $IC_{50}$ value for each set of replicates on the plate. The template also calculates Z' from the positive and negative control, reports the Hill Slope for each curve, and displays the curve-fit. The $K_i$ is calculated according to the equation:

Compound $K_i = [I]_{50}/([L]_{50}/K_d + [P]_0/K_d + 1)$ where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, and $K_d$ represents the dissociation constant of the FITC-MLL or 10mer-Thr-FAM probe for WDR5.

Serum-Shift FPA Assay:

The FPA or TR-FRET assay may be evaluated in the presence of 1-10% fetal calf to ascertain non-specific binding to albumin. Compounds with high levels of non-specific protein binding should display higher $IC_{50}$ values for displacement of the labeled probe and thus less potent $K_i$ values.

Anti-Proliferative Activity Using MLL-Harboring and Non-MLL Cell Lines.

MV4:11, Molm 13, K562, and HL-60 cells are grown in RPMI-1640 media supplemented with 10% FBS and 1% penicillin/streptomycin. Viability assays are performed by dispensing 5,000 cells into each well of an opaque 96-well plate and adding compounds at the indicated concentrations in a final volume of 100 μL and a final concentration of DMSO of 0.1% for all samples. After a set incubation period, either a 3 day or 7 day protocol, the viability of cells in each well is assessed using the CellTiter-Glo assay (Promega), read on a GloMax 96 Microplane Luminometer (Promega). Serial dilutions of each cell type are included in all assays to generate standard curves and determine assay measurements are taken within the dynamic range of the instrument. $GI_{50}$ values are calculated based on three biological replicates, each with three technical replicates. Data are expressed as mean plus/minus S.E.M.

TABLE 2

FPA and TR-FRET binding affinity of representative WDR5 WIN-site inhibitors.

| Example | $K_i$ (M) |
|---|---|
| B1 | 6.93E−07 |
| B2 | 1.38E−06 |
| B3 | 3.02E−08 |
| B4 | 1.91E−08 |
| B5 | 2.70E−08 |
| B6 | 3.35E−09 |
| B7 | 3.30E−08 |
| B8 | 2.10E−08 |
| B9 | 9.00E−08 |
| B10 | 7.09E−08 |
| B11 | 2.66E−09 |
| B12 | 8.38E−09 |
| B13 | 1.74E−08 |
| B14 | 2.68E−08 |
| B15 | 2.37E−09 |
| B16 | 7.16E−09 |
| B17 | 3.62E−08 |
| B18 | 1.43E−08 |
| B19 | 1.72E−07 |
| B20 | 9.56E−08 |
| B21 | 2.29E−08 |
| B22 | 4.26E−07 |
| B23 | 7.69E−07 |
| B24 | 3.30E−08 |
| B25 | 7.10E−07 |
| B26 | 1.85E−08 |
| B27 | 7.30E−07 |
| B28 | 1.69E−07 |
| B29 | 9.02E−10 |
| B30 | 3.75E−06 |
| B31 | 8.35E−07 |
| B32 | 5.68E−07 |
| B33 | 2.22E−08 |

TABLE 3

Growth inhibitory activity of representative WDR5 WIN-site inhibitors in MV4,11 human leukemia cells after a 7 day incubation.

| Example | $GI_{50}$ (nM) |
|---|---|
| B11 | 8.89E−06 |
| B12 | 1.72E−05 |
| B14 | 2.23E−05 |
| B29 | 7.25E−06 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I),

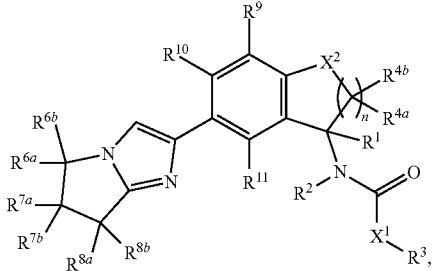

or a pharmaceutically acceptable salt thereof, wherein:

$R^1$ is hydrogen or $C_{1-4}$alkyl;

$R^2$ is hydrogen, $C_{1-6}$alkyl, $C_{3-8}$cycloalkyl, or $C_{3-8}$cycloalkyl-$C_{1-3}$alkylene-;

$X^1$ is a bond;

$R^3$ is $G^1$ or -$L^1$-$G^2$;

$G^1$ and $G^2$ are $C_{3-8}$cycloalkyl, 4- to 8-membered heterocyclyl, aryl, or heteroaryl, wherein $G^1$ and $G^2$ are optionally substituted with 1-5 substituents independently selected from the group consisting of halogen, cyano, $C_{1-4}$alkyl, $C_{1-4}$haloalkyl, —O—$C_{1-4}$alkyl, —O—$C_{1-4}$haloalkyl, OH, oxo, —C(O)$C_{1-4}$alkyl, —C(O)$C_{1-4}$haloalkyl, —NH$_2$, —NH($C_{1-4}$alkyl), —N($C_{1-4}$alkyl)$_2$, —NHC(O)$C_{1-4}$alkyl, and —N($C_{1-4}$alkyl)C(O)$C_{1-4}$alkyl;

$L^1$ is —$C_{1-3}$alkylene-;

$R^{4a}$, at each occurrence, is independently hydrogen, halogen, cyano, $C_{1-4}$alkyl, $C_{1-4}$haloalkyl, —O—$C_{1-4}$alkyl, or OH;

$R^{4b}$, at each occurrence, is independently hydrogen, halogen, or $C_{1-4}$alkyl; or $R^{4a}$ and $R^{4b}$ together with the carbon to which they are attached form a $C_{3-6}$cycloalkyl;

n is 1 or 2;

$X^2$ is $C(R^{4a})(R^{4b})$ or $N(R^5)$;

$R^5$ is hydrogen, $C_{1-4}$alkyl, $C_{1-4}$haloalkyl, $C_{3-6}$cycloalkyl, $C_{3-6}$cycloalkyl-$C_{1-3}$alkylene-, —C(O)$C_{1-4}$alkyl, —C(O)$C_{3-6}$cycloalkyl, or —C(O)O$C_{1-4}$alkyl;

$R^{6a}$, $R^{6b}$, $R^{7a}$, $R^{7b}$, $R^{8a}$, and $R^{8b}$ are each hydrogen; and $R^9$, $R^{10}$, and $R^{11}$ are each hydrogen.

2. The compound of claim 1, or a pharmaceutically acceptable salt thereof, wherein $R^{4a}$ and $R^{4b}$ are each hydrogen.

3. The compound of claim 2, or a pharmaceutically acceptable salt thereof, wherein $R^1$ is hydrogen.

4. The compound of claim 1, or a pharmaceutically acceptable salt thereof, wherein n is 1.

5. The compound of claim 1, or a pharmaceutically acceptable salt thereof, wherein n is 2.

6. The compound of claim 1, or a pharmaceutically acceptable salt thereof, wherein $X^2$ is $CH_2$.

7. The compound of claim 1, or a pharmaceutically acceptable salt thereof, wherein $X^2$ is $NR^5$.

8. The compound of claim 7, or a pharmaceutically acceptable salt thereof, wherein $R^5$ is —C(O)$C_{1-4}$alkyl.

9. The compound of claim 1, or a pharmaceutically acceptable salt thereof, wherein $R^2$ is hydrogen or $C_{3-8}$cycloalkyl-$C_{1-3}$alkylene-;

$G^1$ is
  a 4- to 8-membered heterocyclyl containing one heteroatom selected from nitrogen, oxygen, and sulfur; phenyl; or
  a 5- to 6-membered monocyclic heteroaryl; and $G^2$ is phenyl;

wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl.

10. The compound of claim 2, or a pharmaceutically acceptable salt thereof, wherein $R^2$ is hydrogen or $C_{3-8}$cycloalkyl-$C_{1-3}$alkylene-;

$G^1$ is
  a 4- to 8-membered heterocyclyl containing one heteroatom selected from nitrogen, oxygen, and sulfur; phenyl; or
  a 5- to 6-membered monocyclic heteroaryl; and $G^2$ is phenyl;

wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl.

11. The compound of claim 1, or a pharmaceutically acceptable salt thereof, wherein $G^1$ is 4- to 8-membered heterocyclyl, aryl, or heteroaryl; and $G^2$ is aryl; wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl.

12. The compound of claim 11, or a pharmaceutically acceptable thereof, wherein:

$G^1$ is:
  a 4- to 8-membered heterocyclyl containing one heteroatom selected from nitrogen, oxygen, and sulfur; phenyl; or
  a 5- to 6-membered monocyclic heteroaryl; and $G^2$ is phenyl;

wherein $G^1$ and $G^2$ are optionally substituted with 1-5 substituents independently selected from the group consisting of halogen, $C_{1-4}$alkyl, $C_{1-4}$haloalkyl, —O—$C_{1-4}$alkyl, OH, —C(O)$C_{1-4}$alkyl, —C(O)$C_{1-4}$haloalkyl, and —NHC(O)$C_{1-4}$alkyl.

13. The compound of claim 3, or a pharmaceutically acceptable salt thereof, wherein $R^2$ is hydrogen or $C_{3-8}$cycloalkyl-$C_{1-3}$alkylene-;

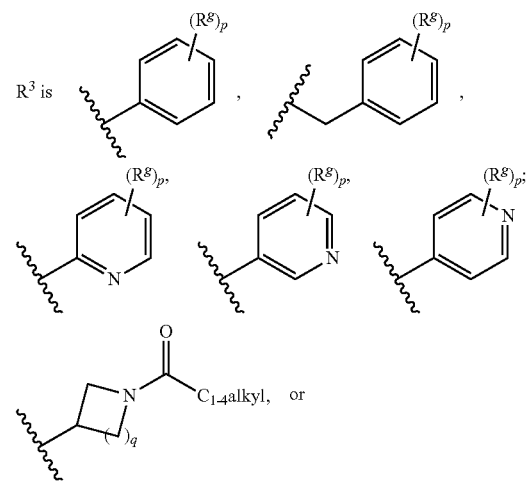

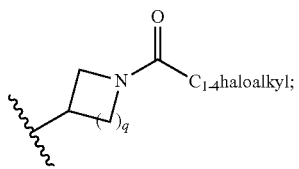
R$^g$ is halogen, C$_{1-4}$alkyl, C$_{1-4}$haloalkyl, —O—C$_{1-4}$alkyl, OH, or —NHC(O)C$_{1-4}$alkyl;
p is 1-3; and
q is 1-4.
14. The compound of claim 13, or a pharmaceutically acceptable salt thereof, wherein R$^3$ is:
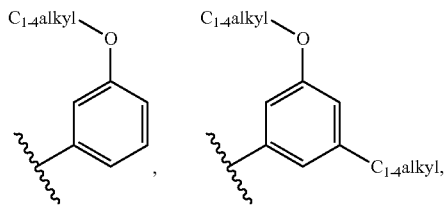
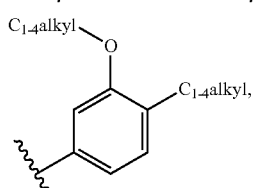
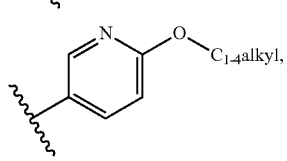
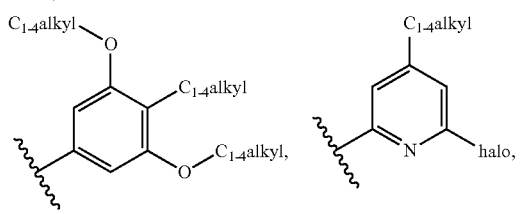
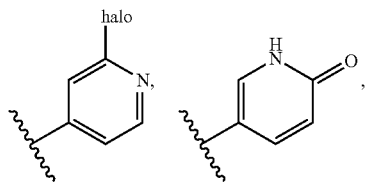
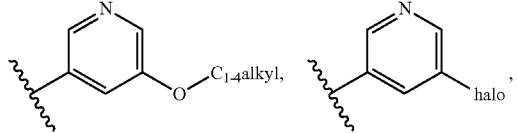
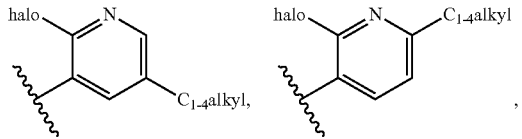
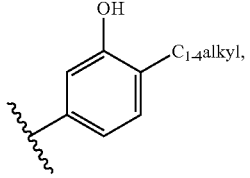
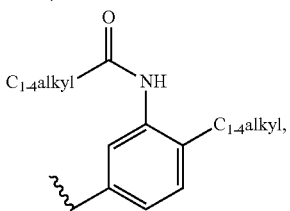
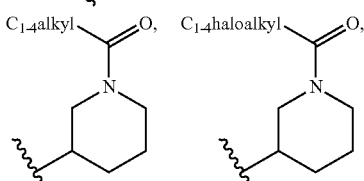
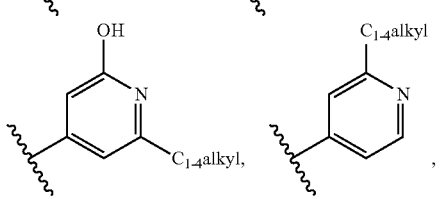
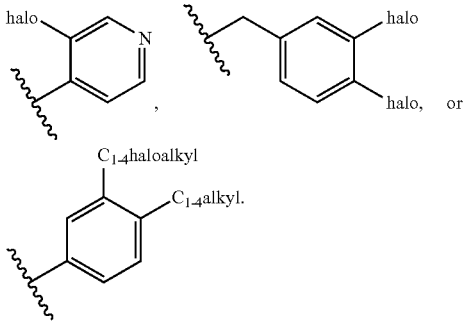
15. The compound of claim 13, or a pharmaceutically acceptable salt thereof, wherein R$^3$ is:
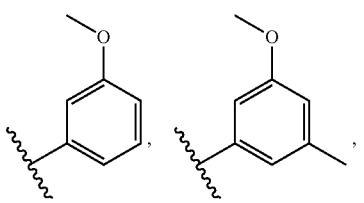
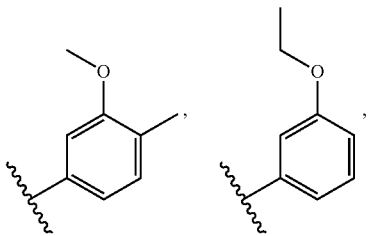

-continued

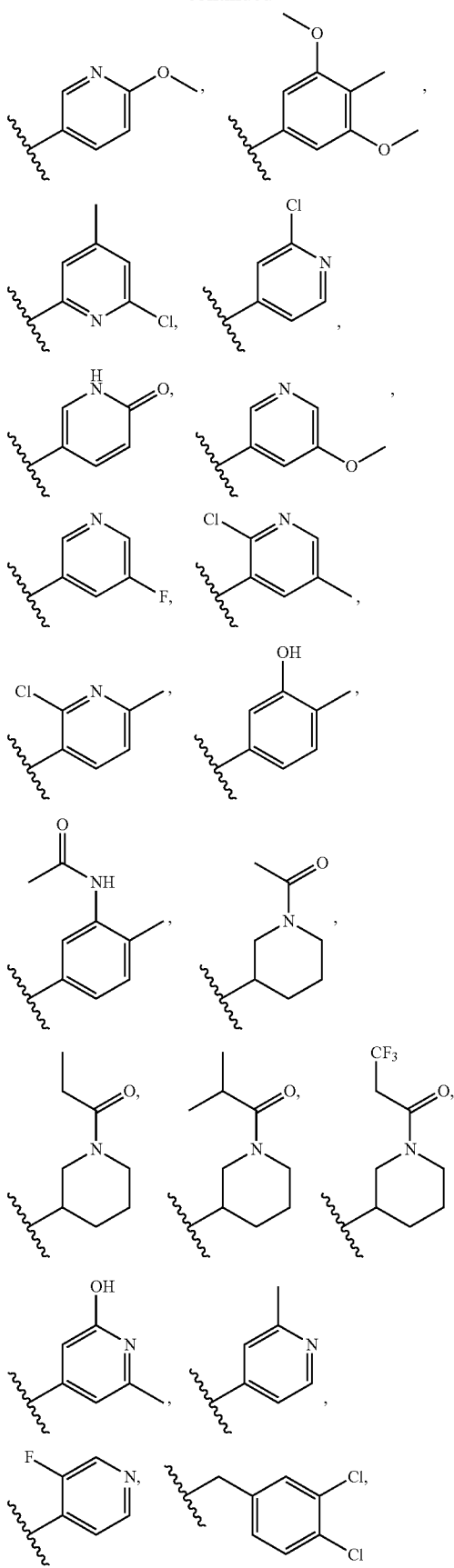

-continued

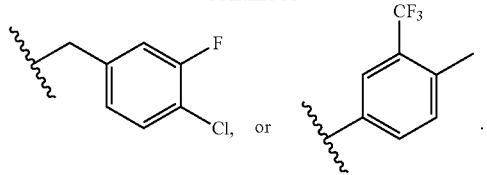

16. The compound of claim 15, having formula (I-a):

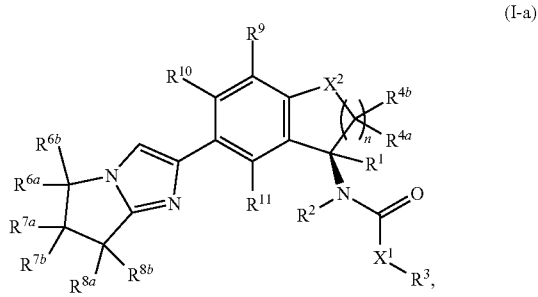

or a pharmaceutically acceptable salt thereof.

17. The compound of claim 1, selected from the group consisting of
N-(cyclopropylmethyl)-N-(6-(6,7-dihydro-5H-pyrrolo[1,2-a]imidazol-2-yl)-2,3-dihydro-1H-inden-1-yl)-3-methoxybenzamide;
N-(6-(6,7-dihydro-5H-pyrrolo[1,2-a]imidazol-2-yl)-2,3-dihydro-1H-inden-1-yl)-4-methyl-3-(trifluoromethyl)benzamide;
N-(6-(6,7-dihydro-5H-pyrrolo[1,2-a]imidazol-2-yl)-2,3-dihydro-1H-inden-1-yl)-3-methoxy-4-methylbenzamide;
N-(6-(6,7-dihydro-5H-pyrrolo[1,2-a]imidazol-2-yl)-2,3-dihydro-1H-inden-1-yl)-3-ethoxybenzamide;
N-(6-(6,7-dihydro-5H-pyrrolo[1,2-a]imidazol-2-yl)-2,3-dihydro-1H-inden-1-yl)-3-methoxy-5-methylbenzamide;
2-(3,4-dichlorophenyl)-N-(6-(6,7-dihydro-5H-pyrrolo[1,2-a]imidazol-2-yl)-2,3-dihydro-1H-inden-1-yl)acetamide;
1-acetyl-N-(6-(6,7-dihydro-5H-pyrrolo[1,2-a]imidazol-2-yl)-2,3-dihydro-1H-inden-1-yl)piperidine-3-carboxamide;
N-(6-(6,7-dihydro-5H-pyrrolo[1,2-a]imidazol-2-yl)-2,3-dihydro-1H-inden-1-yl)-1-propionylpiperidine-3-carboxamide;
N-(6-(6,7-dihydro-5H-pyrrolo[1,2-a]imidazol-2-yl)-2,3-dihydro-1H-inden-1-yl)-1-(3,3,3-trifluoropropanoyl)piperidine-3-carboxamide;
N-(6-(6,7-dihydro-5H-pyrrolo[1,2-a]imidazol-2-yl)-2,3-dihydro-1H-inden-1-yl)-1-isobutyrylpiperidine-3-carboxamide;
(R)-2-(3,4-dichlorophenyl)-N-(6-(6,7-dihydro-5H-pyrrolo[1,2-a]imidazol-2-yl)-2,3-dihydro-1H-inden-1-yl)acetamide;
(R)—N-(6-(6,7-dihydro-5H-pyrrolo[1,2-a]imidazol-2-yl)-2,3-dihydro-1H-inden-1-yl)-3-methoxy-4-methylbenzamide;
1-acetyl-N—((R)-6-(6,7-dihydro-5H-pyrrolo[1,2-a]imidazol-2-yl)-2,3-dihydro-1H-inden-1-yl)piperidine-3-carboxamide;

(R)—N-(7-(6,7-dihydro-5H-pyrrolo[1,2-a]imidazol-2-yl)-1,2,3,4-tetrahydronaphthalen-1-yl)-3-methoxy-4-methylbenzamide;

(R)-2-(4-chloro-3-fluorophenyl)-N-(6-(6,7-dihydro-5H-pyrrolo[1,2-a]imidazol-2-yl)-2,3-dihydro-1H-inden-1-yl)acetamide;

N—((R)-6-(6,7-dihydro-5H-pyrrolo[1,2-a]imidazol-2-yl)-2,3-dihydro-1H-inden-1-yl)-1-propionylpiperidine-3-carboxamide;

1-acetyl-N—((R)-7-(6,7-dihydro-5H-pyrrolo[1,2-a]imidazol-2-yl)-1,2,3,4-tetrahydronaphthalen-1-yl)piperidine-3-carboxamide;

N—((R)-7-(6,7-dihydro-5H-pyrrolo[1,2-a]imidazol-2-yl)-1,2,3,4-tetrahydronaphthalen-1-yl)-1-propionylpiperidine-3-carboxamide;

(R)—N-(6-(6,7-dihydro-5H-pyrrolo[1,2-a]imidazol-2-yl)-2,3-dihydro-1H-inden-1-yl)-6-methoxynicotinamide;

(R)-2-chloro-N-(6-(6,7-dihydro-5H-pyrrolo[1,2-a]imidazol-2-yl)-2,3-dihydro-1H-inden-1-yl)isonicotinamide;

(R)-2-chloro-N-(6-(6,7-dihydro-5H-pyrrolo[1,2-a]imidazol-2-yl)-2,3-dihydro-1H-inden-1-yl)-5-methylnicotinamide;

(R)—N-(6-(6,7-dihydro-5H-pyrrolo[1,2-a]imidazol-2-yl)-2,3-dihydro-1H-inden-1-yl)-6-methyl-2-oxo-1,2-dihydropyridine-4-carboxamide;

(R)-6-chloro-N-(6-(6,7-dihydro-5H-pyrrolo[1,2-a]imidazol-2-yl)-2,3-dihydro-1H-inden-1-yl)-4-methylpicolinamide;

(R)—N-(6-(6,7-dihydro-5H-pyrrolo[1,2-a]imidazol-2-yl)-2,3-dihydro-1H-inden-1-yl)-2-methylisonicotinamide;

(R)—N-(6-(6,7-dihydro-5H-pyrrolo[1,2-a]imidazol-2-yl)-2,3-dihydro-1H-inden-1-yl)-3-hydroxy-4-methylbenzamide;

(R)—N-(6-(6,7-dihydro-5H-pyrrolo[1,2-a]imidazol-2-yl)-2,3-dihydro-1H-inden-1-yl)-5-methoxynicotinamide;

(R)-3-acetamido-N-(6-(6,7-dihydro-5H-pyrrolo[1,2-a]imidazol-2-yl)-2,3-dihydro-1H-inden-1-yl)-4-methylbenzamide;

(R)-2-chloro-N-(6-(6,7-dihydro-5H-pyrrolo[1,2-a]imidazol-2-yl)-2,3-dihydro-1H-inden-1-yl)-6-methylnicotinamide;

(R)—N-(6-(6,7-dihydro-5H-pyrrolo[1,2-a]imidazol-2-yl)-2,3-dihydro-1H-inden-1-yl)-3,5-dimethoxy-4-methylbenzamide;

(R)—N-(6-(6,7-dihydro-5H-pyrrolo[1,2-a]imidazol-2-yl)-2,3-dihydro-1H-inden-1-yl)-3-fluoroisonicotinamide;

(R)—N-(6-(6,7-dihydro-5H-pyrrolo[1,2-a]imidazol-2-yl)-2,3-dihydro-1H-inden-1-yl)-6-oxo-1,6-dihydropyridine-3-carboxamide;

(R)—N-(6-(6,7-dihydro-5H-pyrrolo[1,2-a]imidazol-2-yl)-2,3-dihydro-1H-inden-1-yl)-5-fluoronicotinamide; and (R)—N-(1-acetyl-6-(6,7-dihydro-5H-pyrrolo[1,2-a]imidazol-2-yl)-1,2,3,4-tetrahydroquinolin-4-yl)-3-methoxy-4-methylbenzamide, or a pharmaceutically acceptable salt thereof.

18. A pharmaceutical composition comprising the compound of claim 1, or a pharmaceutically acceptable salt thereof, and a pharmaceutically acceptable carrier.

19. A method of inhibiting the binding of mixed lineage leukemia 1 (MLL1) to WD40 repeat protein 5 (WDR5) in a patient with cancer comprising administering to the subject, a therapeutically effective amount of the compound of claim 1, or a pharmaceutically acceptable salt thereof.

20. The method of claim 19, wherein the cancer is selected from the group consisting of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

* * * * *